US005571418A

United States Patent [19]

Lee et al.

[11] Patent Number: 5,571,418

[45] Date of Patent: Nov. 5, 1996

[54] HEMOFILTRATION OF TOXIC MEDIATOR-RELATED DISEASE

[76] Inventors: Patrice A. Lee, 2425 Winona Dr., Plano, Tex. 75074; James R. Matson, 7826 Mason Dells Dr., Dallas, Tex. 75023; Robert W. Pryor, 3341 Sage Brush Trail, Plano, Tex. 75023

[21] Appl. No.: 271,136

[22] Filed: Jul. 6, 1994

Related U.S. Application Data

[63] Continuation-in-part of Ser. No. 109,750, Aug. 20, 1993, abandoned.

[51] Int. Cl.[6] .......................... B01D 61/00; B01D 61/14; A61M 1/38

[52] U.S. Cl. .................... 210/651; 210/500.41; 210/645; 210/650; 604/4; 604/5; 604/6

[58] Field of Search .................................... 210/645, 650, 210/651, 767, 500.41; 604/4, 5, 6; 436/177, 178; 530/412, 414

[56] References Cited

U.S. PATENT DOCUMENTS

| | | | |
|---|---|---|---|
| 4,229,291 | 10/1980 | Walch et al. | 210/646 |
| 4,402,940 | 9/1983 | Nose et al. | 210/645 |
| 4,874,522 | 10/1989 | Okamoto et al. | 210/645 |
| 4,966,709 | 10/1990 | Nosé et al. | 210/651 |

OTHER PUBLICATIONS

Patricia A. Lee et al., Critical Care Medicine, vol. 21, No. 6, pp. 914–924 (Jun. 1993).

W. F. Koller et al., "CAVH in Acute Respiratory Failure," Int. Conf. on CAVH, Aachen 1984, pp. 96–102 (Karger, Basel 1985).

G. Zobel et al., Intensive Care Med, 17:315–319 (1991).

F. Coraim et al., "CAVH after Cardiac Surgery", Int. Conf. on CAVH, Aachen 1984, pp. 116–124 (Karger, Basel 1985).

Paul Sporn et al., First Vienna Shock Forum, Part B, pp. 225–233 (1987).

*Primary Examiner*—John Kim

*Attorney, Agent, or Firm*—Fulbright & Jaworski L.L.P.

[57] ABSTRACT

The present invention provides methods of treating pathophysiological states characterized by the presence in blood of certain toxic mediators. The novel method of hemofiltration of the present invention provides an effective treatment of several such disease including sepsis, shock, acute renal failure, multiple organ system failure and systemic inflammatory response syndrome-related diseases.

8 Claims, 5 Drawing Sheets

* Data From *Crit Care Med* 21(6):914-924, 1993

† p<0.02 vs. 50K Filter HF 400
‡ p<0.01 vs. 50K Filter HF 250 (Nonfiltered)

† 50kD Filter p< 0.05 vs. Time

HEMOFILTRATION OF TOXIC MEDIATOR-RELATED DISEASE

CROSS REFERENCE TO RELATED APPLICATIONS

This is a continuation-in-part of U.S. patent application Ser. No. 08/109,750, filed Aug. 20, 1993, now abandoned.

BACKGROUND OF THE INVENTION

1. Field of the Invention

The present invention relates generally to methods of hemofiltration. More specifically, the present invention relates to a novel method of hemofiltration for toxic mediator-related diseases.

2. Description of the Related Art

Medical illness, trauma, complication of surgery, i.e., any human disease state, if sufficiently injurious to the patient, may elicit the Systemic Inflammatory Response Syndrome (SIRS). SIRS within physiologic limits is beneficial, i.e., promoting removal of dead tissue, healing of injured tissue and mobilization of host defenses to resist or combat infection. If the stimulus to SIRS is too potent, e.g., as a result of massive tissue injury or microbial sepsis, then the SIRS may be extreme. The resulting excessive inflammation is injurious or destructive to vital organ tissue resulting in vital organ dysfunction or failure. This is recognized clinically as multi-organ system failure (MOSF). Depending on the number of organ systems failing, MOSF has a mortality rate of 40–100%. In the USA each year, MOSF results in about 150,000 deaths, afflicts 400–600,000 patients, and adds billions of dollars of cost to the nation's health care.

Critical care medicine techniques available to manage SIRS-MOSF are entirely supportive. There is no definitive therapy. The mechanism of SIRS is the excessive release of host derived inflammatory mediators, referred to in this context as toxic mediators (TM). TM include various cytokines (tumor necrosis factor, TNF; the interleukins; interferon), various prostaglandins (PG $I_2$, $E_2$, Leukotrienes), various clotting factors (platelet activating factor, PAF), various peptidases, reactive oxygen metabolites, and various poorly understood peptides which cause organ dysfunction (myocardial depressant factor, MDF). These compounds interact in a cascade fashion with many augmenting the inflammatory response. Some are directly injurious to tissue (MDF, peptidases), others promote destructive inflammation (cytokines). Infection (abscesses, sepsis) is a common complication of critical illness. Certain bacterial exotoxins, endotoxins or enterotoxins are extremely potent stimuli to SIRS. Sepsis is the single most common cause of SIRS leading to MOSF. The development and use of effective antibiotics and other supportive measures have had no effect on the death rate from MOSF.

Hemofiltration (HF) was developed as a technique to control overhydration and acute renal failure in unstable intensive care unit (ICU) patients. The technique of HF involves a hemofilter. The hemofilter consists of a woven membrane (polysulfone, polyamide, etc.) fabricated as either a parallel plate or hollow fiber filtering surface. The blood path to, through, and from the membrane is low resistance so the patients' own blood pressure drives blood through the filter circuit. The pores of most filter membranes will allow passage of molecules up to 30,000 Daltons with very few membranes allowing passage of molecules up to 50,000 Daltons. The membranes were built to achieve the following specific goals. First, to permit high conductance of the aqueous phase of blood plasma water needed to permit the formation of ultrafiltrate at a fairly low transmembrane pressure (typically 20–40 mm Hg). This requires a relatively large pore size which incidentally passes molecules of up to 30,000 to 50,000 Daltons. The ultrafiltrate, with current filters, contains electrolytes and small molecules (urea, creatinine, uric acid) but no cells and proteins. The composition of the ultrafiltrate is very similar to plasma water. Second, prior art membranes were designed specifically to avoid passage of albumin (68,000 Daltons). Loss of albumin, and subsequently, oncotic pressure, could cause or aggravate tissue edema and organ dysfunction (e.g., pulmonary edema).

During filtration of protein containing solutions, colloids or suspensions, the accumulation of protein as a gel or polarization layer occurs on the membrane surface. This gel layer typically reduces effective pore size, reducing the filterable molecular weights by roughly 10–40%. Therefore, pore sizes selected are somewhat larger than needed, anticipating a reduction in effective size. Thus, present membranes allow filtration and removal of excess water, electrolytes, small molecules and nitrogenous waste while avoiding any loss of albumin or larger proteins. These membranes are well-suited to their accepted uses, that is, treatment of overhydration and acute renal failure.

The hemofilter is part of a blood circuit. In passive flow HF, arterial blood flows through a large bore cannula, into plastic tubing leading to the filter; blood returns from the filter through plastic tubing to a vein. This is known as arteriovenous HF. Alternately, a blood pump is used so that blood is pumped from a vein to the filter and returned to a vein or venovenous HF. Ultrafiltrate collects in the filter jacket and is drained through the ultrafiltrate line and discarded.

Current membranes, when used to treat acute renal failure associated with MOSF have been associated with incidental improvements in organ function other than the kidneys. However, these membranes remain deficient in the treatment of MOSF because their specific design characteristics prevent them from removing TM in the upper molecular weight range of recognized TM.

The prior art remains deficient in the lack of effective methods of treating toxic mediator-related disease by hemofiltration. The present invention fulfills this long-standing need and desire in this art.

SUMMARY OF INVENTION

In one embodiment of the present invention, there is provided a novel method of continuous arteriovenous hemofiltration using a polysulfone or similar material, hollow fiber hemofilter with a molecular weight exclusion limit of up to 100,000 to 150,000 Daltons as therapeutic regimen for sepsis, multiple organ failure (MOF), systemic inflammatory response syndrome (SIRS) or other mediator-related diseases. In a preferred embodiment, the present invention provides a procedure comprising 1) pumped arteriovenous or venovenous hemofiltration using hemofilters, with 2) a molecular weight exclusion of up to 100,000 to 150,000 Daltons for 3) mediator-related disease.

In another embodiment of the present invention, there is provided a method of treating a pathophysiological state by hemofiltering blood, comprising the steps of: withdrawing blood from a mammal; filtering the blood; removing an ultrafiltrate of plasma; and returning said blood to the mammal.

Other a further objects, features and advantages will be apparent form the following description of the present preferred embodiments of the invention which are given for the purpose of disclosure when taken in conjunction with the accompanying drawings.

BRIEF DESCRIPTION OF THE DRAWINGS

The drawings are not necessarily to scale. Certain features of the invention may be exaggerated in scale or shown in schematic form in the interest of clarity and conciseness.

DETAILED DESCRIPTION OF THE INVENTION

Figure 1:
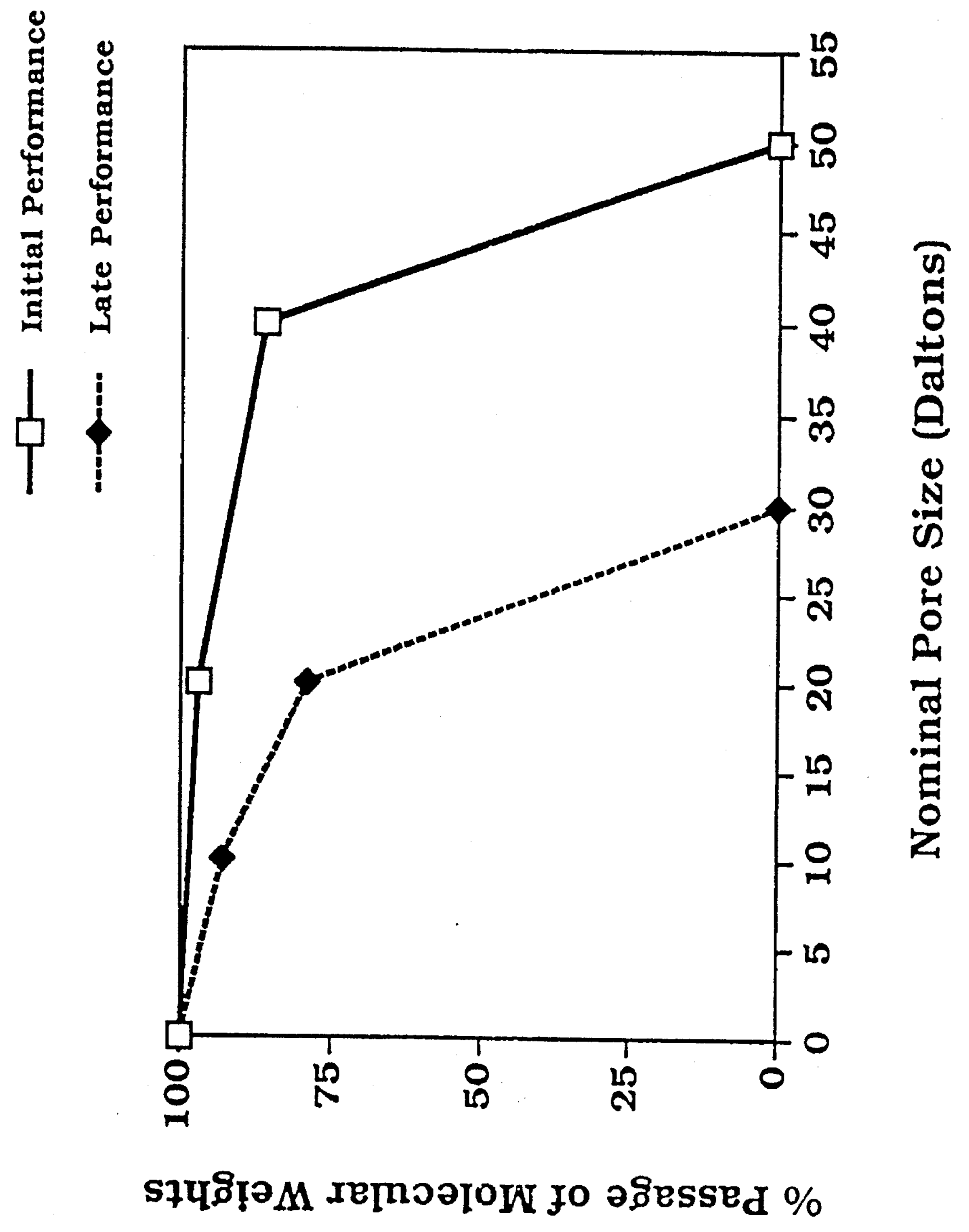
FIG. 1 shows that as the effective molecular weight limit of a pore size is approached, the percentage passed through of progressively larger toxic mediator molecules progressively declines.

It will be readily apparent to one skilled in the art that various substitutions and modifications may be made to the invention disclosed herein without departing from the scope and spirit of the invention.

The present invention comprises a HF method using a novel membrane fabricated with a pore size capable of allowing passage of molecules up to 100,000 to 150,000 Daltons. The methods of the present invention are useful in treating human patients with SIRS-MOSF. The membrane useful in the methods of the present invention provides for removal by filtration of the entire known range of TM.

Definitions

As used herein, the term "hemofiltration" refers to a process of filtering blood by a membrane with separation of all formed elements, all proteins larger than effective pore size, and retained plasma water and solute (these return to the patient) from ultrafiltrate.

As used herein, the term "ultrafiltrate" refers to the filtered plasma water and solute and molecules (including target peptides and proteins) smaller than effective pore size.

As used herein, the term "SIRS or Systemic Inflammatory Response Syndrome" refers to the excessive and dysfunctional elaboration by a human patient of inflammatory mediators which results in an excessive and injurious inflammatory response.

As used herein, the term "MOSF or Multiple Organ System Failure" refers to the clinical syndrome of vital organ dysfunction or failure due to tissue injury resulting from SIRS. Its mortality rate is 40–100%.

As used herein, the term "TM or Toxic Mediators" refers to a heterogeneous group of chemicals synthesized and released by human tissue. TM include the inflammatory mediators of SIRS (cytokines, prostaglandins, oxygen metabolites), various clotting factors, various peptidases and various toxic peptides. The molecular weight range of known TM is 1,000–60,000.

As used herein, the term "Hemofilter" refers to the filter used in hemofiltration. It is configured as either a series of parallel plates or as a bundle of hollow fibers. The blood path is from a blood inlet port, through the fibers or between the plates, then to a blood outlet port. Filtration of blood occurs at the membrane with ultrafiltrate forming on the side of the membrane opposite the blood. This ultrafiltrate accumulates inside the body of the filter contained and embodied by the filter jacket. This jacket has an ultrafiltrate drainage port.

As used herein, the term "Extracorporeal Circuit" refers to the system of plastic tubes attached to the hemofilter which is used clinically. The arterial line is the plastic tube which carries blood from artery or vein to the blood inlet port of the hemofilter. The venous line carries blood from the blood outlet port returning to a vein. The ultrafiltrate line carries ultrafiltrate from the ultrafiltrate drainage port on the filter jacket to a reservoir from which ultrafiltrate is discarded.

As used herein, the term "effective sieving coefficient" refers to the physical property of a membrane to exclude or pass molecules of a specific molecular weight. For the purposes of the present invention, the appropriate membrane allows for passage of molecules in the range of toxic mediators (up to 60,000 to 70,000 Daltons) in the presence of whole blood/blood proteins.

The present invention provides a method of treating a pathophysiological state by filtering blood, comprising the steps of: withdrawing blood from a mammal; filtering the blood; removing an ultrafiltrate of plasma; and returning said blood to the mammal. The methods of the present invention may use either continuous arteriovenous or continuous venovenous hemofiltration.

Generally, the methods of the present invention may be used to treat pathophysiological states characterized by the presence in the blood of certain toxic mediators. The methods of the present invention may preferably be used to treat sepsis, acute renal failure, acute respiratory failure, shock, multiple organ failure and systemic inflammatory response syndrome. Representative examples of toxic mediators are interleukin 1, interleukin 2, tumor necrosis factor, bacterial toxins, leukotrienes, prostaglandin $E_2$ and prostaglandin $I_2$.

In the methods of the present invention, blood is filtered by contacting said blood with the filter membrane. Preferably, the filter has an effective sieving coefficient of about 1.0 for said toxic mediators. In addition, the filter has a molecular weight exclusion limit of up to 100,000 to 150,000 Daltons.

The following examples are given for the sole purpose of illustrating various embodiments of the present invention and are not meant to limit the present invention in any fashion.

EXAMPLE 1

Animal Model of MOSF Induced by *S. aureus*

Procedural rules and standards of AAALAC and good laboratory practice were used in all animal handling and experimentation. Immature swine (*Sus scrofa;* Poland China Breed) between 4–10 kg in weight and 4–8 weeks of age were studied. Following anesthesia (ketamine, valium) and instrumentation, *Staphylococcus aureus* (*S. aureus;* ATCC

#49496) in a dose of $8.0\times10^9$ CFU/kg was infused over one hour. *S. aureus* organisms were prepared according to standard methods well known in the art. This dose in this breed is 100% lethal with a mean time of death of 27+5 hours.

A hemofilter with a pore size permitting passage of molecules of 50,000 Daltons or less was used. Blood was drawn from a femoral artery into the arterial limb of the extracorporeal circuit, then to hemofilter, then to the venous limb of the extracorporeal circuit and returned through a femoral vein. A roller pump was used on the arterial limb to assure constant and/or known blood flow within and between experiments. Ultrafiltrate (UF) was drained through the ultrafiltrate drain line to a closed sterile reservoir on ice. UF was collected every two hours and frozen at –40° C. The UF drain line passed through a gated intravenous fluid pump to assure constant UF flow rate.

More specifically, the animals were fasted for 12 hours, brought to the laboratory, anesthetized with ketamine and valium (or lorazepam). Using sterile technique, vascular catheters were placed in the femoral arteries, femoral veins, and a peripheral vein. An endotracheal tube was placed to prevent airway obstruction, animals breathed room air spontaneously. A 30 minute equilibration period (from T–0.5 hr to T–0 hr) was allowed. Then, the *S. aureus* was infused over one hour from time (T) zero to one hour (T+1). From T+1 hr to T+7 hrs, blood was pumped through the extracorporeal circuit. At T+7 hrs the blood pump was stopped and blood returned to the animal. From T–0.5 hr to T+10 hrs the animals were monitored continuously for heart rate, blood pressure, core temperature, and intermittently for arterial pH, $PCO_2$, $PO_2$, and various biochemical and hematologic parameters. Standard laboratory methods were used for measuring hematologic and biochemical parameters.

At T+10 hrs, all vascular catheters were removed, wounds closed and anesthesia stopped. The endotracheal tube was removed when the pigs were awake. Pigs were observed until death or T+168 hrs (seven days) survival. The time of death was noted and an necropsy performed. If the animal lived 168 hours, it was regarded as a permanent survivor; euthanitized with a barbiturate overdose and necropsied. No antibiotics were given at any time.

Paired, identically prepared pigs-randomly assigned as one control and one experimental pig-were used. The experimental pig underwent pumping (RenalFlo Mini-Pump, Minntech, Inc., Minneapolis, Minn.) of blood through the extracorporeal circuit with concomitant hemofiltration (RenalFlo HF250 hemofilter). Ultrafiltrate was replaced volumetrically and concurrently with Ringer's lactate infused into the venous limb. This was done to maintain isovolemia. The control pig underwent pumping of blood through the extracorporeal circuit with hemofiltration blocked by occlusively clamping the ultrafiltrate drain line. Both animals received maintenance fluids as normal saline at 100 ml/kg/day. Anticoagulation was done with heparin with a loading dose was 100 IU/kg followed by an initial maintenance dose of 40 IU/kg/hr. This was adjusted to maintain partial thromboplastin time at about two times control values. It has been previously shown that circulation of blood from septic animals through simple plastic tubing with return to the animal results in a modest, but significant, increase in survival. Thus, to isolate the hemofiltration of TM as the effect of interest, animals were maintained isovolemic, and all exposed to the same blood extracorporeal circuit, hemofilter, blood pump tubing and pumping procedure.

Three groups were studied, differing in rate of extracorporeal circuit blood flow and ultrafiltrate flow rate. Therefore, each group had a different filtration fraction. Filtration fraction (FF) was calculated by dividing ultrafiltrate flow rate by extracorporeal circuit blood flow rate. FF is an approximate indicator of efficiency of plasma water removal. FF also is an approximate index of the tendency of the membrane to form a protein polarization layer. This layer can affect removal of molecules by reducing effective pore size (reduces removal of molecules in selected molecular weight range) or enhancing absorption (increasing effective removal).

TABLE I

Hemofiltration Groups

| Group | Blood Flow (ml/min) | Ultrafiltrate Flow (ml/min) | FF (%) |
|---|---|---|---|
| I | 150 | 8.3 | 5.5 |
| II | 50 | 8.3 | 16.7 |
| III | 50 | 16.7 | 33.4 |

TABLE II

Survival Time (hrs) From T-0 Until Death or Seven Days

| Group | I | II | III |
|---|---|---|---|
| Filtered | 53.0 ± 10.2 | 96.0 ± 9.3 | 70.0 + 3.8 |
| Non-Filtered | 33.3 + 6.8 | 48.8 + 3.8 | 17.0 + 4.8 |
| % Increment in Survival | 57% | 97% | 312% |
| p Value* | <0.03 | <0.001 | <0.001 |

*Mantel-Haenszel Chi-Squared Analysis

Tables I and II show that survival time was longer in filtered pigs than in non-filtered, control pigs. Survival time appears to increase with increasing FF. Thus, increased removal of TM increases survival. At necropsy, filtered animals had less tissue hemorrhage and congestion; nearly dry lungs but more abscesses. Death in filtered pigs appeared to result from destruction of lung tissue by abscess formation instead of pulmonary edema and hypoxemia, as in filtered pigs. In summary, pigs which were filtered survived longer and had less tissue congestion and hemorrhage than those that were not filtered.

EXAMPLE 2

Removal of Pathophysiologic Factors

The ultrafiltrate (UF) collected on ice from pigs in Example 1 was frozen at –40° C. The volume of UF from each pig was either 3 liters (Groups I & II) or 6 liters (Group III). Each pig's ultrafiltrate was thawed and filtered through a benchtop system (Millipore Pellicon Cassette System, effective pore size retaining molecules 1,000 Dalton or greater). The filtrate from this process, containing molecules less than 1,000 Dalton was discarded. The retentate was processed until it was 10% of its original volume, i.e., 300 ml for UF from Groups I & II or 600 ml for UF from Group III. This retentate should contain molecules from 1,000 Dalton to 50,000 Dalton (i.e., the largest molecule passed by the HF250 hemofilter). All retentate fluids (RF) obtained from septic pigs were cultured and were sterile. A separate group of pigs was prepared as in Example 1, were not given *S. aureus*, but were hemofiltered to produce "clean" ultrafiltrate. All these pigs recovered from the procedure and remained well until euthanitized at seven days. The clean ultrafiltrate was filtration condensed as described above to produce clean retentate fluid (CRF). The CRF was sterile.

Weaned pigs of the same age, breed, weight, and sex distribution described Example 1 were used. Each was anesthetized, endotracheally intubated, vascularly cannulated and monitored in the same manner as pigs in Example 1. No *S. aureus* was given and no extracorporeal circuit was placed. Each pig received as a six hour infusion (T+0 to T+6 hrs) of either RF or CRF. All CRF recipients (n=4) showed no pathophysiologic changes, recovered promptly from the experiment, and remained well until euthanasia and necropsy at seven days. All necropsies were normal. All RF recipients developed progressive hypoxemia and pulmonary edema. Death rates and times are tabulated.

TABLE III

| Source of SRF | # of Survivors at 7 Days | Average Time of Death* |
|---|---|---|
| I | 2/8 | 33.0 ± 27.0 |
| II | 2/6 | 88.0 ± 34.0 |
| III | 3/6 | 114.0 ± 31.0 |

*If a pig survived 168 hours and was euthanitized for necropsy, then 168 hours was used as that pig's time of death.

At necropsy, RF recipients had tissue congestion and hemorrhage indistinguishable from that seen in *S. aureus* pigs. The following findings appeared in RF recipients and were not present in *S. aureus* recipients: (1) no abscesses; (2) massive flabby myocardial dilatation; (3) ascites with viable gram negative enteric organisms, e.g., evidence of translocation.

In summary, RF reproduces the pathologic, morbid, and mortal feature of *S. aureus* sepsis. This demonstrates that factors, most probably TM, responsible for sickness and death in *S. aureus* sepsis, are removed by filtration.

Hemofilters in usual operation undergo membrane polarization with a 10–40% reduction in effective pore size. Hemofiltration with a membrane with a nominal pore size allowing passage of 50,000 Dalton molecules significantly improved survival time in a model of lethal *S. aureus* sepsis. The sterile RF obtained from these pigs reproduces the lethal multi-organ failure seen with *S. aureus,* indicating that pivotal TM's are filtered. With the anticipated decrement in effective pore size, the largest molecular weight of TM's removed by filtration would be 30,000 to 45,000, i.e., as much as 50% of the known molecular weight range (1,000–51,000 Dalton) of TM was not removed by the prior art membrane. While improvements were obtained with the prior art membrane, there remains a need for an improved method for controlling the TM response.

EXAMPLE 3

Increases in survival time were obtained using a commonly available membrane with a 50,000 Dalton pore size. However, all animals did eventually die, albeit by a somewhat different apparent mechanism—lung destruction by abscess formation rather than organ dysfunction from TM release. Also, all essential features of *S. aureus* sepsis in this model could be reproduced by infusion of sterile RF indicating that pivotal TM in the cascade had been removed by the current membrane, albeit not the entire molecular weight range of known TM.

The present invention increases the pore size of the HF membrane which is otherwise fabricated from the same or similar materials using the same or similar techniques as existing HF membranes. The rationale for this invention derives from what is to be filtered and its internal characteristics, and how the filtration process occurs. What is to be filtered is the complete known molecular weight range of TM. The molecular weight range of recognized TM is shown in Table IV.

TABLE IV

Molecular Size of Mediators

| Type | Molecular Weight (Daltons) |
|---|---|
| C3a | 9000 |
| C5a | 11000 |
| PG's; Leukotriens & Thromboxane | <1000 |
| PAF | ? |
| Microbial Toxins | 10000 or greater |
| MDS/MDF | 10000 to 30000 |
| Interleukins | 4000 to 25000 |
| Interferons | 40000 to 70000 |
| Myeloid Growth Factors | 19000 to 90000 |
| Tumor Necrosis Factor (Trimer) | 51000 |

These TM function in cascade fashion. The cascade sequence is shown in Table 5, progressing from the top down, with earlier TM stimulating synthesis of later TM. Individual steps in the cascade may exhibit any or all of the following characteristics.

TABLE V

1. Stimulate target cells to synthesize next TM or TM's
2. Augment earlier steps.
3. Agonist and/or antagonist function on target cells
4. Stimulation of more than one step in the cascade
5. The cascade seems to recur in cycles.
6. Its internal system of positive feedback is only partially understood.

To reliably control this cascade with its known and unknown positive feedback loops, requires that all its elements be removed. The filtration process occurs at the membrane pore. The membrane and pores exhibit the following characteristics: (1) membrane materials exhibit an electric charge; (2) pores exhibit characteristic shape and dimensions (cross section, length) depending on the material and fabrication process;(3) factors #1 & #2 are altered by the formation of a protein polarization layer on the membrane surface (see below): (4) factors #1 & #2 determine the nominal pore size; and factor #3 determines effective pore size which usually decreases progressively with membrane use as polarization layer accumulates; (5) molecules to be filtered exhibit, in addition to molecular weight, a geometry determined by their tertiary and quaternary structures, and a charge. As molecules approach molecular weight limits of effective pore size, charge and shape have increasingly important effects on whether or not they will pass through a pore. Molecules charged similarly to the pore boundaries will be repelled. Elongated molecules may nor may not pass through depending on their orientation to the pore. The aggregate effect of #1–5 is shown in the FIG. 1. Thus, as the effective molecular weight limit of a pore size is approached, the percentage passed through of these progressively larger molecules, progressively declines. Finally, the largest molecule of recognized TM is tumor necrosis factor (trimeric, biologically active form) with a molecular weight of 51,000. To effectively filter TNF and the other TM, a membrane with a nominal pore size about 40% larger than TNF is needed, i.e., an effective pore size of 100,000 Dalton or greater.

The only approved use of HF is for overhydration and acute renal failure. The molecular weight range of target molecules is shown in the Table 6.

TABLE VI

| Component | MW (Daltons) |
|---|---|
| $H_2O$ | 10.00 |
| K | 19.00 |
| Na | 11.00 |
| Urea | 60.06 |
| Creatine | 113.12 |
| Urate | 210.19 |
| $PO_4$ | 47.00 |

Even allowing for decrements in effective pore size, most hemofilters have an excessively large pore size for the target molecules of acute renal failure. The reason for this is to provide the greatest possible flux of water for the low transmembrane pressures at which these membranes often operate. The upper limit of a pore size is that which totally excludes albumin (68,000 Dalton). In acute renal failure and other critical illnesses, albumin concentration is inversely related to mortality rate. Thus, any loss of albumin through the filter theoretically could increase patient risk of death unless albumin were replaced. This would add significantly to the cost of HF, as well as tax an already limited resource (human albumin, a blood product). Thus, filtration of albumin has been categorically avoided for economic and safety reasons, as well as no need to work in that molecular weight range, i.e., >50,000 Dalton.

The present invention allows passage of all known TM which will allow down modulation of the excessive and destructive inflammatory response which ameliorates MOSF. Any risk of albumin loss will be offset by albumin replacement and improved patient morbidity and mortality from MOSF.

EXAMPLE 4

Efficacy Of 100,000 Dalton Hemofilter

Weaned pigs of the same age, breed, weight, and sex distribution described Example 1 were used. Each was anesthetized, endotracheally intubated, vascularly cannulated and monitored in the same manner as pigs in Example 1. Experiments were performed in pairs (7 animals per filter group; 2 groups; N=14). Each animal received a one hour infusion of *S. aureus* ($8\times10^9$ CFU/kg) over one hour from time (T) zero to one hour (T+1). From T+1 hr to T+7 hrs, hemofiltration was performed. One of the pair of pigs was filtered with the 50,000 Dalton filter and the other with the 100,000 Dalton filter. At T+7 hrs the blood pump was stopped and blood returned to the animal. From T–0.5 hr to T+10 hrs the animals were monitored continuously for heart rate, blood pressure, core temperature, and intermittently for arterial pH, $PCO_2$, $PO_2$, and various biochemical and hematologic parameters.

At T+10 hrs, all vascular catheters were removed, wounds closed and anesthesia stopped. The endotracheal tube was removed when the pigs were awake. Pigs were observed until death or T+168 hrs (seven days) survival. The time of death was noted and an necropsy was done. Animals surviving 168 hours were regarded as permanent survivors; were euthanitized with a barbiturate overdose and necropsied. No antibiotics were given at any time.

As in Example 1, ultrafiltrate was replaced volumetrically and concurrently with Ringer's lactate infused into the venous limb of the extracorporeal circuit. Anticoagulant (heparin) was given as in Example 1. The hemofiltration procedure was performed with the following circuit function parameters: Blood Flow=100 ml/min; UF flow 16.7 ml/min; pumped arteriovenous with post-filter fluid replacement.

Figure 2:
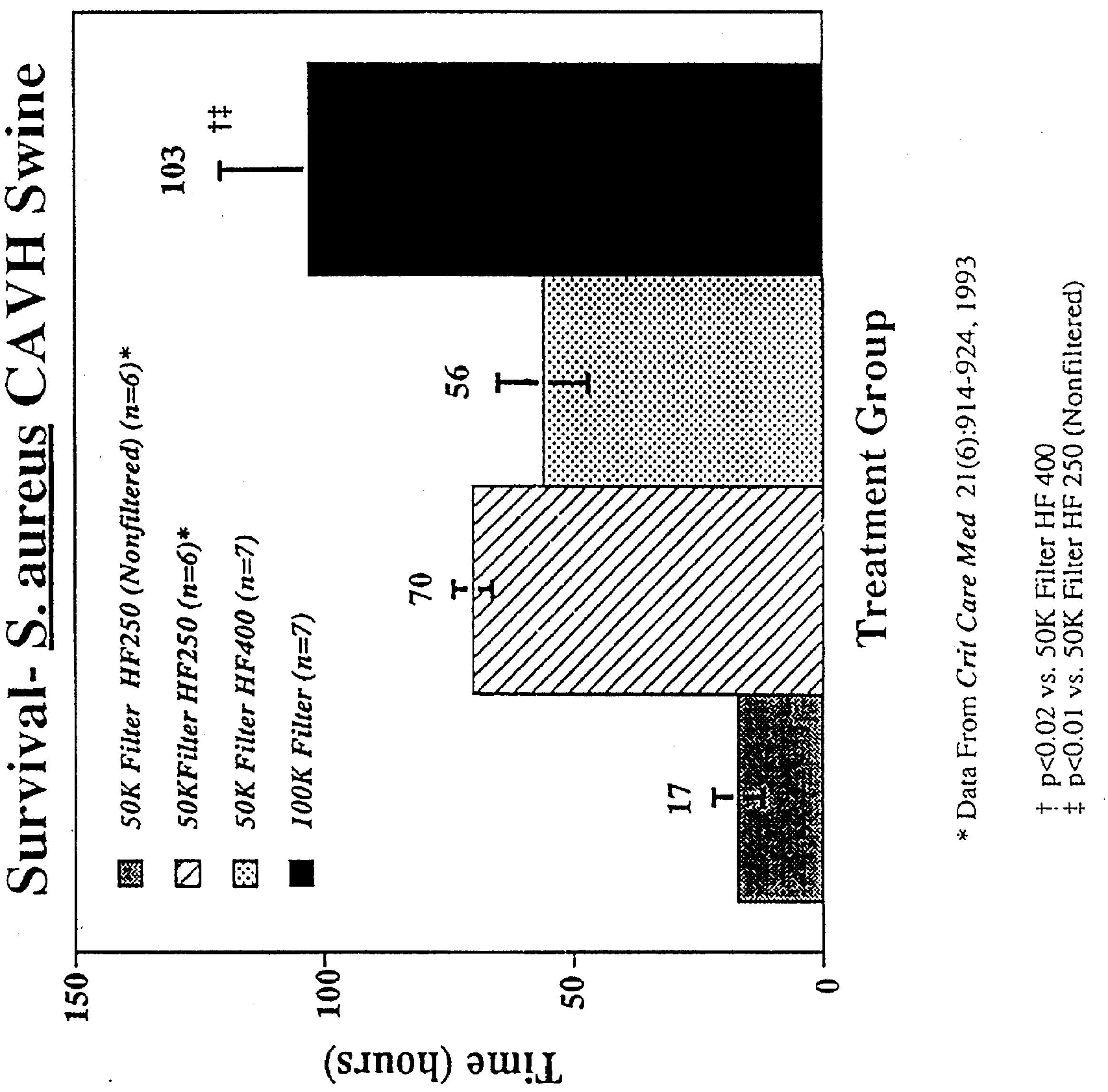
FIG. 2 shows that the 100,000 Dalton filter [vs. prior art filters (50,000 Daltons)] significantly enhances survival in an immature swine model of lethal *Staphylococcus aureus* sepsis.
Figure 3:
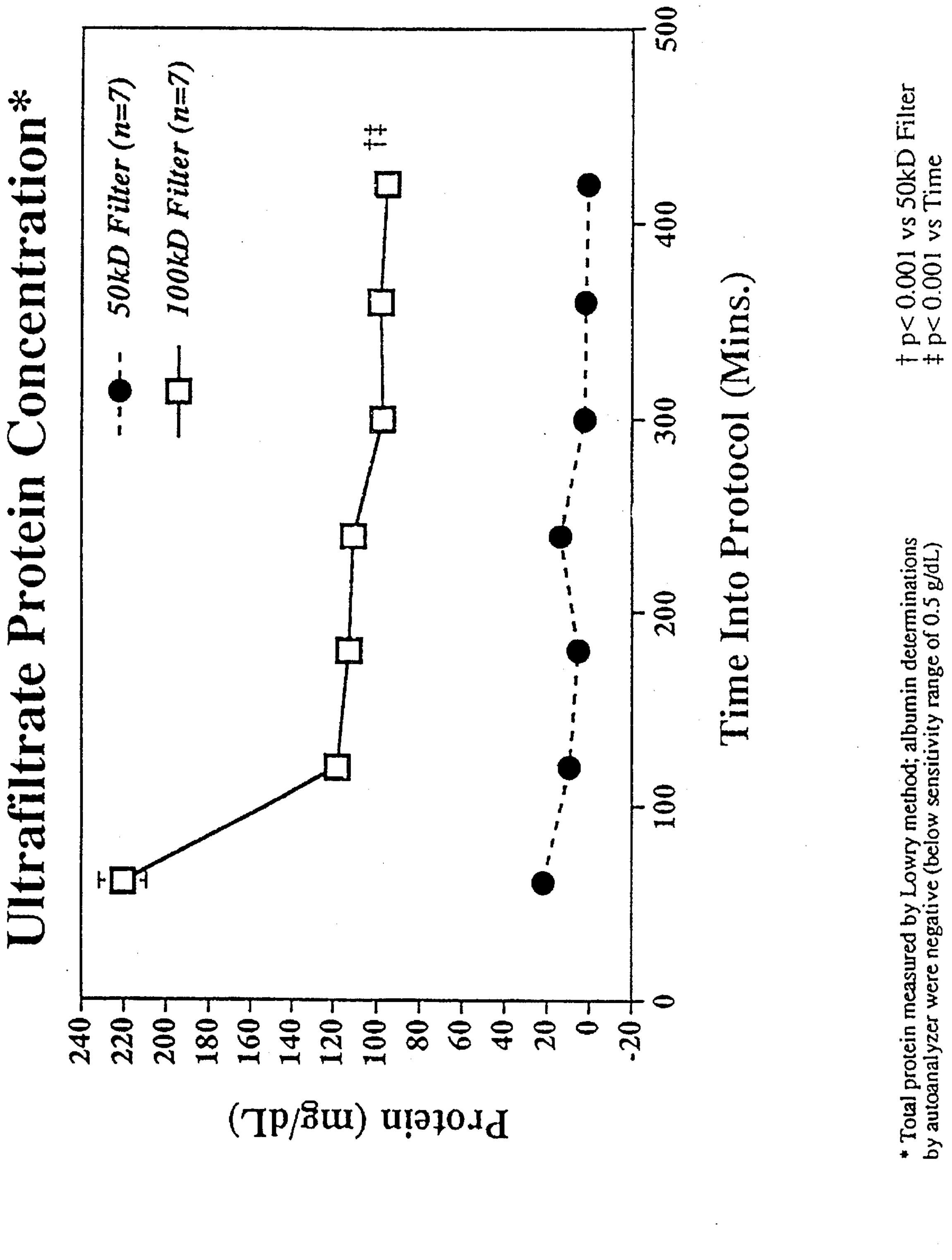
FIG. 3 shows that the 100,000 Dalton filter removes significantly more protein than prior art filters (50,000 Dalton).
Figure 4:
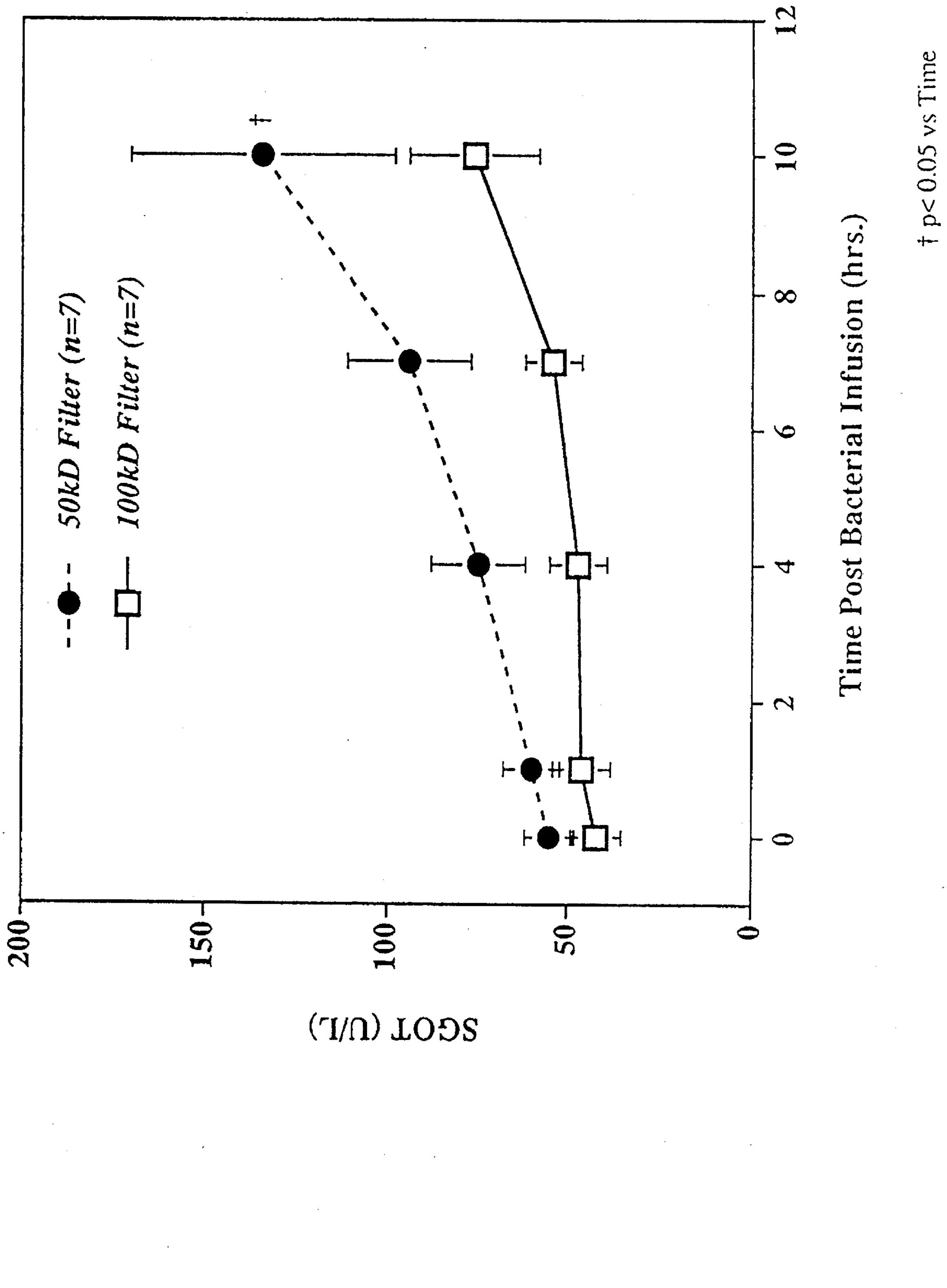
FIG. 4 shows that the 100,000 Dalton filter is significantly more effective than prior art filters (50,000 Dalton) in reducing early serum indicators of liver damage (SGOT) normally associated with this model of sepsis.
Figure 5:
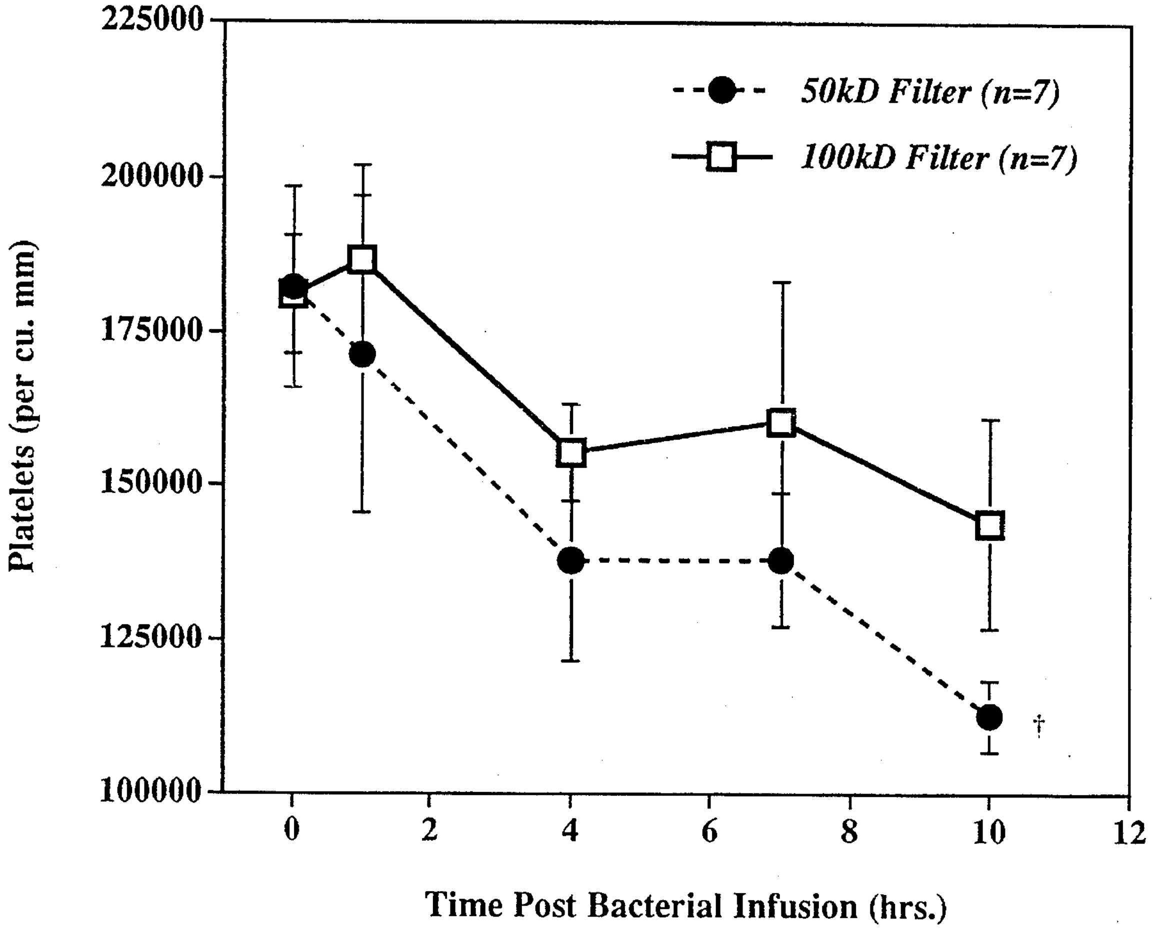
FIG. 5 shows that the 100,000 Dalton filter is significantly more effective than prior art filters (50,000 Dalton) in reducing early signs of coagulation abnormalities (platelet count) normally associated with this model of sepsis.

FIG. 2 shows the survival times for the two treatment groups. Animal filtered with the 100 kD filter survived significantly longer than animals filtered with 50 kD filter. FIG. 3 shows that the 100 kD filter removed ten-fold more protein than the 50 kD filter. Albumin was not detected in ultrafiltrate samples from either treatment group. Ultrafiltrate albumin concentration probably was below the lower sensitivity level of the autoanalyzer (0.5 g/dL). Liver failure and coagulation disorders are associated with mediator-related disease states. As shown in FIGS. 4 and 5, animals treated with the 50 kD filter had a significant increase in serum glutamic oxaloacetic transaminase (SGOT; indicative of early liver damage) and a significant decrease in platelet count. Changes in these parameters among animals treated with the 100 kD filter were not significantly different over time.

CAVH therapy, in general, improves morbidity and mortality in this swine model of lethal *S. aureus* sepsis. HF with the 100 kD filter is superior to HF with the 50 kD filter in a) improving mortality and b) blunting early indicators of organ failure normally associated with this model of sepsis. We conclude that the 100 kD filter is more effective at removing larger molecular weight toxic mediators that are released in this septic response.

What is claimed:

1. A method of treating a pathophysiological state caused by a toxic mediator-related disease consisting of hemofiltering blood with a filter, wherein said filter has a molecular weight exclusion limit of 100,000 to 150,000 Daltons and allows for passage of molecules with a molecular weight of about 70,000 Daltons in the presence of whole blood.

2. The method of claim 1, wherein said hemofiltering of blood consists of the steps of:

withdrawing blood from a mammal;

filtering the blood to remove an ultrafiltrate of plasma thereby providing filtered blood; and returning said filtered blood to the mammal.

3. The method of claim 1, wherein said hemofiltering is selected from the group consisting of continuous arteriovenous hemofiltration and continuous venovenous hemofiltration.

4. The method of claim 1, wherein said pathophysiologic state is selected from the group consisting of sepsis, shock, multiorgan system failure and systemic inflammatory response syndrome.

5. The method of claim 1, wherein filtration removes a toxic mediator with a molecular weight ≦60,000 Daltons.

6. The method of claim 5, wherein said filter has an effective sieving coefficient of 0.5 to 1.0 for toxic mediators with a molecular weight of≦60,000 Daltons.

7. The method of claim 5, wherein said toxic mediator is selected from the group consisting of interleukins, tumor necrosis factor, bacterial toxins, leukotrienes, prostaglandins, growth factors and tissue factors.

8. The method of claim 1, wherein said filter is a polysulfone filter.

* * * * *